United States Patent
Clarén et al.

(10) Patent No.: US 6,379,315 B1
(45) Date of Patent: Apr. 30, 2002

(54) SPATULA FOR TAKING OF SAMPLING

(75) Inventors: Jan Clarén, Lund; Nils Stormby, Malmö, both of (SE)

(73) Assignee: Medscand Medical AB, Malmo (SE)

( * ) Notice: Subject to any disclaimer, the term of this patent is extended or adjusted under 35 U.S.C. 154(b) by 0 days.

(21) Appl. No.: 09/647,500

(22) PCT Filed: Mar. 30, 1999

(86) PCT No.: PCT/SE99/00513

§ 371 Date: Nov. 29, 2000

§ 102(e) Date: Nov. 29, 2000

(87) PCT Pub. No.: WO99/52443

PCT Pub. Date: Oct. 21, 1999

(30) Foreign Application Priority Data

Apr. 1, 1998 (SE) .............................................. 9801141

(51) Int. Cl.[7] .............................................. A61B 10/00
(52) U.S. Cl. ...................................... 600/570; 606/160
(58) Field of Search ................................ 600/562, 570, 600/569, 572; 606/160, 161

(56) References Cited

U.S. PATENT DOCUMENTS

| 2,471,088 | A |   | 5/1949  | Ayre ........................ 600/570 |
| 3,315,661 | A | * | 4/1967  | Groat ....................... 600/570 |
| 3,592,186 | A |   | 7/1971  | Oster ....................... 600/570 |
| 3,774,590 | A | * | 11/1973 | McDonald .................. 600/570 |
| 4,016,865 | A | * | 4/1977  | Fredricks .................. 600/570 |
| 4,384,587 | A | * | 5/1983  | Milgrom .................... 600/570 |
| 4,932,957 | A | * | 6/1990  | Zwick ....................... 606/160 |
| 4,981,143 | A | * | 1/1991  | Sakita et al. ............... 600/570 |
| 5,092,345 | A |   | 3/1992  | Sakita ....................... 600/570 |
| 6,171,323 | B1 | * | 1/2001 | Potti et al. ................. 606/161 |

FOREIGN PATENT DOCUMENTS

| DE |    37 90 193 |   | 6/1990 |            |
| EP |    0 050 632 |   | 5/1982 |            |
| GB |    1 429 689 |   | 3/1976 |            |
| SU |    1424802 A | * | 9/1988 | ...... 600/562 |

OTHER PUBLICATIONS

"Surgical Instruments", J. Sklar Mfg. Co., Inc., 18th Edition, 1973.*

* cited by examiner

Primary Examiner—Eric F. Winakur
Assistant Examiner—Charles Marmor, II
(74) Attorney, Agent, or Firm—Merchant & Gould, P.C.

(57) ABSTRACT

A spatula for sampling comprises an elongated stem (10) having a flat scraper at least at one end of the stem. According to the invention said scraper is perforated.

21 Claims, 2 Drawing Sheets

SPATULA FOR TAKING OF SAMPLING

Figures 1, 2:
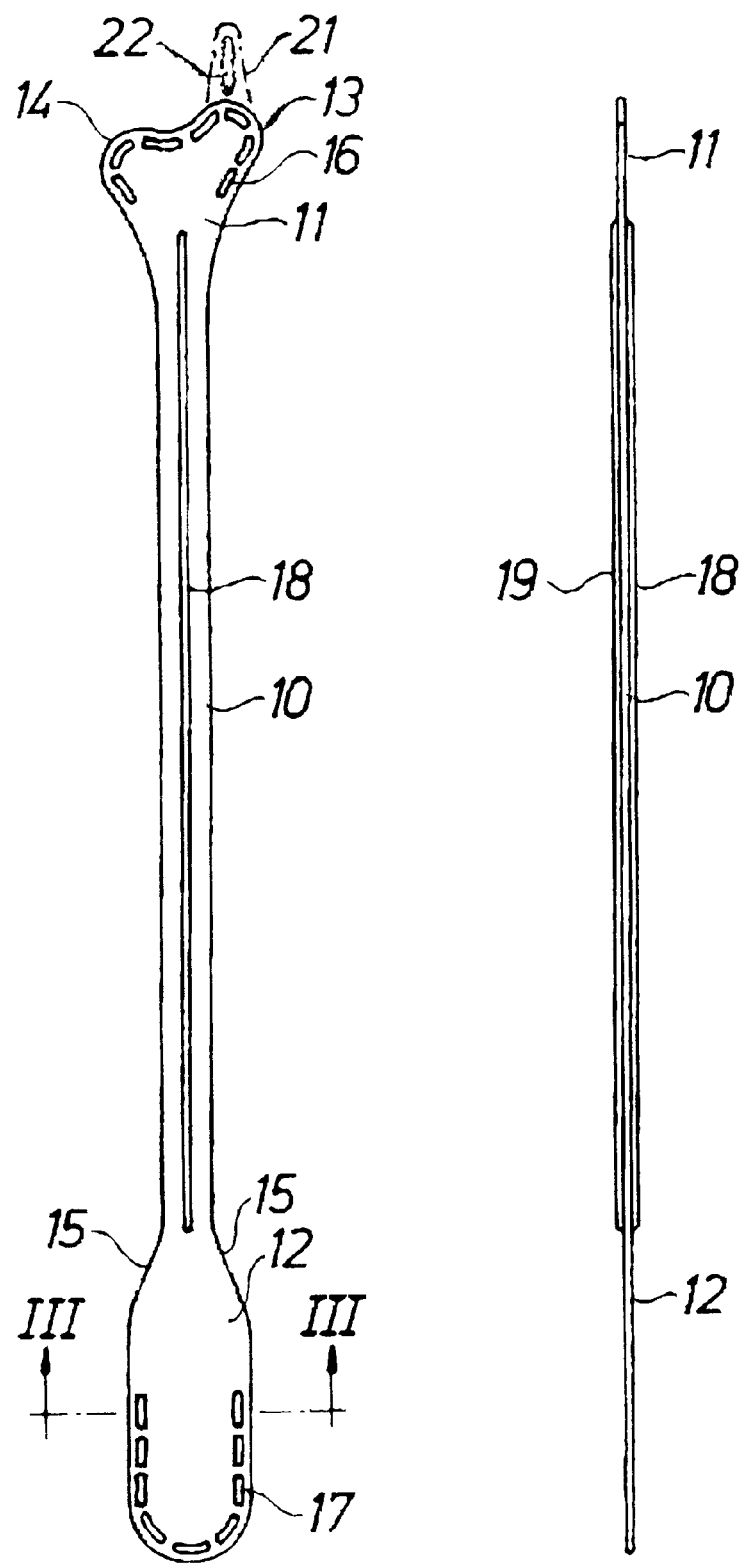

The invention relates to a spatula for sampling which comprises an elongated stem having a flat scraper at least at one end of the stem.

The spatula according to the invention has been invented particularly for biological sampling i.e. collection of cells and secretion (mucus) for example in the region of ectocervix, for examination of the taken cell sample. However, the invention is not limited to a spatula for this special type of sampling; the spatula can also be used for other kinds of sampling e.g. from the oral cavity, the throat, or other mucous membranes.

A spatula for sampling from the ectocervix is shown and described in GB-B-1 429 689. In the embodiment described therein the scraper forms three lobes one lobe thereof projecting axially from one end of the stem, the other two projecting each at one side of the axial lobe transversely of the stem. The other end of the stem forms a handle for the manipulation of the spatula at sampling from the ectocervix. Then, the central lobe is introduced into the external os, and the spatula is rotated at least one turn, cells and secretion being scraped from the uterine cervix and the endocervical canal in the region of the external os where cellular changes by experience appear initially at developing cancer. The cellular sample can be transferred from the spatula to a slide by the sample being smeared directly onto the slide, being fixed and stained in order then to be examined in a microscope (so called Papanicolau test or Pap smear), or the spatula can instead be immersed into a transport solution wherein the cellular sample is washed off the spatula in order then to be transported with the transport solution to a laboratory where the cellular sample by means of different preparation techniques is transferred to a slide for manual or computer controlled examination in a microscope. It is of course important at such sampling that the cellular sample is retained on the spatula up to the smearing or washing, respectively, which has been observed in U.S. Pat. No. 3,592,186 which relates to an instrument for collecting cells for cytological examination, said instrument comprising a stem having a scraper at one end and a handle at the other end. The scraper being substantially heart-shaped with two projecting lobes, a longer one and a shorter one, the axes of which are perpendicular to each other. In this document it is recommended that the inherently hydrophobic surface of the scraper presents a rough structure. This can be achieved by a suitable treatment of the surface, but there are also materials which inherently have a suitable surface structure, e.g. some kinds of wood. Wooden spatulas are, however, not suitable for sampling for two reasons: firstly, it is difficult to smear the cellular sample onto a slide because the wooden spatula is too stiff, and, secondly, the cellular material will be sucked into the wooden spatula which has a hydrophilic surface so that the taken cellular sample partly adheres to the spatula. As a consequence thereof a smaller amount of cellular material will be deposited onto the slide.

GB-B-1 429 689 mentions nothing regarding the surface structure of the spatula described therein, which is made of plastic, but in practice spatulas of plastic material for scraping off cellular samples generally have been made with a matted or frosted surface in order to improve the adhesion of the cellular sample to the spatula.

However, it has been found that not even such a surface structure of the scraper provides a satisfactory adhesion. The adhesion perhaps could be improved by increasing the roughness of the matted or frosted surface but this may involve difficulties in smearing the taken cellular sample onto a slide.

EP-B-0 050 632 shows and describes an instrument for sampling from the ectocervix, which in its entirety is injection molded of clear polypropylene and includes an aspirator for sampling by aspirating secretion (mucus) from the endocervical canal, as well as scrapers for collecting cells from the ectocervix. A substantially linear axial through aspiration bore opens at about the centre of the tip of a scraper. In EP-B-0 050 632 the manner in which the sampling is made is illustrated in detail.

DE-C2-37 90 193 discloses an instrument for taking cell samples, having a scraper with parallel through-slits opening in the end edge of the scraper.

According to the invention, the problem to catch by a simple spatula, without aspirator, a sample of viscous character which then easily can be smeared or washed from the spatula, is solved by the spatula of the kind referred to above having obtained the characterizing features of claim 1. By means of the apertures thus provided in the scraper the scraped off sample will be retained on the spatula by capillary action in the apertures, conditioned by the surface tension of the sample, without preventing the cellular sample from being released from the spatula when the sample is being smeared onto a slide or washed off in a transport solution.

Figure 4:
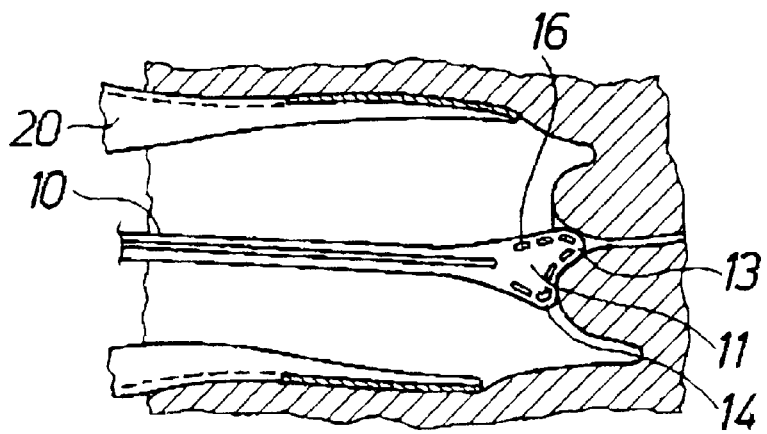
Figure 5:
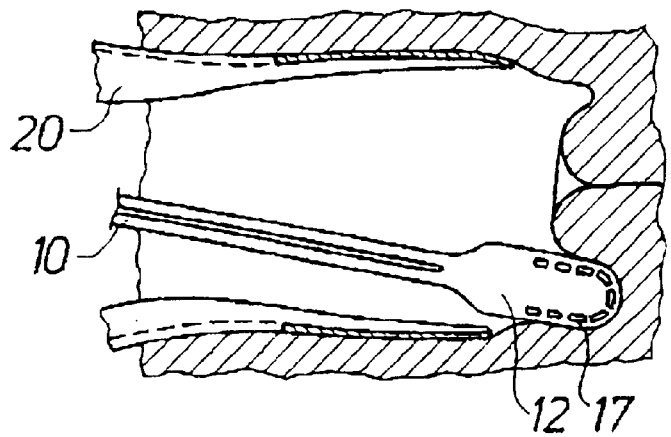

In a presently preferred embodiment of the spatula according to the invention for scraping off and collecting cells at sampling from the ectocervix and the endocervical canal, the apertures are provided inwardly of and along the edge of the scraper. In order to explain the invention this embodiment will be described in more detail, reference being made to the accompanying drawings in which FIG. 1 is a plan view of the spatula, FIG. 2 is a side view thereof, FIG. 3 is an enlarged transverse cross-sectional view taken along line III—III in FIG. 1, FIG. 4 is a fragmentary diagrammatic longitudinal cross-sectional view of a vaginal cavity and discloses the use of the spatula according to FIGS. 1–3 when sampling from the ectocervix, and FIG. 5 is a view similar to FIG. 4, which discloses the use of the spatula according to FIGS. 1–3 when sampling in the uppermost part of the vagina (fornix).

Figure 3:
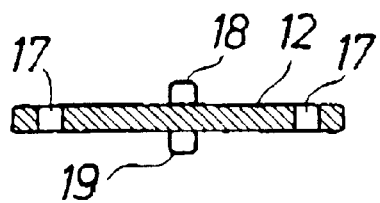

The spatula disclosed in FIGS. 1–3 of the drawing should be made in one piece by injection molding of a suitable plastic material of such kind that the spatula is flexible. The presently preferred material is polypropylene but other plastic materials can be considered, e.g. polyethylene, polyamide (nylon), or polystyrene. The spatula comprises an elongated stem 10 formed as a flat strip of uniform width, which has at one end thereof a flat scraper 11 and at the other end thereof a flat scraper 12, the two scrapers being wider than the stem but have the same thickness as the stem—of the order of 1 mm—and are coplanar with the stem. The scraper 11 is substantially heart-shaped and forms two lobes 13 and 14 projecting at an oblique angle to the longitudinal axis of the stem. The longitudinal axes of the lobes are substantially perpendicular to each other and converge towards and merge on the longitudinal axis of the stem 10. The lobe 13 is longer than the lobe 14, and the two lobes have circularly convex ends. The scraper 12 at the other end of the stem 10 is rectangular with the side edges extending in parallel with the stem and with circularly convex end. It joins the stem at oblique shoulders 15.

Along the edge of the lobes 13 and 14 apertures 16 are provided in the scraper 11 and follow the contour of the edge. The apertures comprise a row of mutually separated slots which can have a width of about 1 mm and a length of about 4 mm. In a similar manner the scraper 12 also comprises a row of mutually separated slots 17 extending along the edge of the scraper 12 but only in the half thereof which is close to the free end of the scraper.

The apertures in the preferred embodiment are formed by slots but within the scope of the invention they can also be formed as circular, triangular, square, or polygonal apertures. The apertures can also be arranged in another manner than along the edge of the scraper but this is the presently preferred embodiment.

The stem 10, at each side of the strip forming the stem, is stiffened by means of a rib 18 and 19, respectively, extending along the center line of the strip over the total length of the stem. These ribs can be replaced by edge flanges provided on the strip so that this is H-shaped in cross-section.

The use of the spatula when sampling from the ectocervix is disclosed in FIG. 4, the scraper 11 being used for the sampling. At the sampling the spatula is introduced into the vagina which is kept widened by means of a speculum 20, and the lobe 13 is engaged with the external os. Then, the spatula is rotated at least one turn so that the two lobes 13 and 14 of the scraper 11 scrape off cells and secretion, i.e. from the external os and the ectocervix. The collected cells together with secretion are retained on the spatula by capillary action in the apertures 17 as mentioned above but can easily be smeared onto a slide or be washed off in a transport solution. The flexibility of the spatula or at least the flat scraper 11 must be adjusted such that the scraper can adapt itself to the anatomic conditions for access to the sampling region and that the cellular sample can be smeared onto the slide, which requires a certain flexibility of the scraper. However, on the other side the flexibility of the spatula in its entirety must not be so great that the stem is too weak and will be twisted when the spatula is rotated during sampling.

By forming an axially projecting tip on the lobe 13 as indicated by a dot-and-dash line 21 in FIG. 1 the sampling from the ectocervix can be combined with sampling from the endocervical canal by the tip 21 being inserted thereinto when the lobe 13 is engaged with the external os. Also the tip 21 should have an aperture and is shown herein with a longitudinal slot 22.

For sampling from the upper part of the vagin (fornix) the scraper 14 is used in the manner shown in FIG. 5. The collected cellular sample is treated as described above.

The invention as to the general scope thereof is not limited to the dimensional figures mentioned above as examples only and relating to the presently preferred embodiment of the spatula for sampling from the ectocervix and the endocervical canal. Another dimensioning and another shape of the flat scraper can be chosen for another type of sampling.

What is claimed is:

1. Spatula for sampling comprising an elongated stem having two ends and a longitudinal axis, the stem having a flat scraper disposed on one end of the stem, the scraper being wider than the stem, the scraper having two flat sides and defining a plurality of apertures for retaining samples by capillary action, extending from one flat side to the other, the apertures being of closed perimeter, the apertures having a shape corresponding to at least one of the group consisting of circular, triangular, square, polygonal, or slotted, the apertures being distributed in a row along an edge of the scraper inwardly of the edge and following a contour of the edge of the scraper.

2. Spatula according to claim 1 wherein the apertures have a width of about 1 mm.

3. Spatula according to claim 2 wherein the apertures have a length of about 4 mm.

4. Spatula according to claim 1 wherein the flat scraper is substantially heart-shaped, the scraper having two lobes having longitudinal axes, the lobes projecting from the stem at oblique angles to the longitudinal axis of the stem, each of the lobes having a circularly convex end.

5. Spatula according to claim 4 wherein a longer of said lobes projects farther than a shorter of said lobes.

6. Spatula according to claim 4 wherein the longitudinal axes of the lobes converge towards and merge on the longitudinal axis of the stem.

7. Spatula according to claim 4 wherein the longitudinal axes of the lobes are perpendicular to each other.

8. Spatula according to claim 4 wherein the longer lobe comprises a tip projecting substantially axially of the stem from the end of said longer lobe.

9. Spatula according to claim 4 further comprising a flat scraper comprising a rectangular shape and a circularly convex end at the other end of the stem.

10. Spatula according to claim 1 wherein the flat scraper comprises a plastic material.

11. Spatula according to claim 10 wherein the spatula is made entirely of a plastic material.

12. Spatula according to claim 10 wherein the plastic material is at least one of the group consisting of polypropylene, polyethylene, polyamide, or polystyrene.

13. Spatula according to claim 1 wherein the stem comprises a flat strip coplanar with said flat scraper, the strip having two sides.

14. Spatula according to claim 13, wherein the strip comprising the stem has a uniform width.

15. Spatula according to claim 13 wherein the strip forming the stem has a thickness equal to a thickness of the scraper.

16. Spatula according to claim 13 wherein at least one side of the strip comprising the stem comprises at least one stiffening rib extending along the strip.

17. Spatula according to claim 16 wherein the strip comprising the stem has a centre line, and wherein both sides of the strip comprise a stiffening rib, the stiffening ribs being disposed along the centre line of the strip.

18. Spatula according to claim 1 wherein at least one side of the flat scraper has a matted surface.

19. Spatula according to claim 18 wherein both sides of the flat scraper have a matted surface.

20. Spatula according to claim 1 wherein the spatula is flexible.

21. Spatula according to claim 1 wherein the flat scraper has a thickness of about 1 mm.

* * * * *